United States Patent
Peng

(10) Patent No.: US 8,298,398 B2
(45) Date of Patent: Oct. 30, 2012

(54) MICRO FLOW DEVICE AND METHOD FOR GENERATING A FLUID WITH PH GRADIENT

(75) Inventor: Chen Peng, Taipei (TW)

(73) Assignee: Benq Materials Corp., Gueishan Township, Taoyuan County (TW)

( * ) Notice: Subject to any disclaimer, the term of this patent is extended or adjusted under 35 U.S.C. 154(b) by 1197 days.

(21) Appl. No.: 12/117,795

(22) Filed: May 9, 2008

(65) Prior Publication Data

US 2009/0321275 A1 Dec. 31, 2009

(30) Foreign Application Priority Data

Jul. 30, 2007 (TW) .............................. 96127851 A

(51) Int. Cl.
*C25B 9/00* (2006.01)
*C25B 1/10* (2006.01)
(52) U.S. Cl. ...................... 205/770; 204/252; 204/275.1
(58) Field of Classification Search .................. 204/253, 204/263, 267, 275, 252, 275.1; 205/770
See application file for complete search history.

(56) References Cited

U.S. PATENT DOCUMENTS

| | | | | |
|---|---|---|---|---|
| 3,497,438 | A | * | 2/1970 | Badgley ......................... 204/548 |
| 5,112,464 | A | * | 5/1992 | Tsou et al. ..................... 204/263 |
| 5,474,662 | A | * | 12/1995 | Miyamae ....................... 204/263 |
| 5,989,402 | A | * | 11/1999 | Chow et al. .................... 204/601 |
| 2006/0169598 | A1 | | 8/2006 | Lee et al. |
| 2007/0068813 | A1 | | 3/2007 | Han et al. |
| 2007/0138025 | A1 | | 6/2007 | Lee et al. |

FOREIGN PATENT DOCUMENTS

| | | |
|---|---|---|
| JP | 2007-171172 | 7/2007 |
| TW | 550234 | 9/2003 |

OTHER PUBLICATIONS

Shoji, S. "Fluids for sensor systems." Topics in Current Chemistry. 1998 (no month). Springer Verlag. vol. 194. pp. 163-188.*
Burns, S.E., Yiacoumi, S., Tsouris, C. "Microbubble generation for environmental and industrial separations." Separation and Purification Technology. vol. 11, Issue 3. Jul. 1997. pp. 221-232.*
P. Marmottant and S. Hilgenfeldt. "A bubble-driven microfluidic transport element for bioengineering." Jun. 29, 2004. Proceedings of the National Academy of Sciences of the United States of America (PNAS). vol. 101, Issue 26. pp. 9523-9527.*

* cited by examiner

*Primary Examiner* — Keith Hendricks
*Assistant Examiner* — Steven A. Friday
(74) *Attorney, Agent, or Firm* — Thomas|Kayden

(57) ABSTRACT

A micro flow device and a method for generating a fluid with pH gradient are provided. The micro flow device includes a first and second substrates, an ion exchange membrane, and at least an electrode unit. The second substrate having a second flow path is disposed corresponding to the first substrate that has a first flow path. The ion exchange membrane is disposed between the first substrate and the second substrate to separate an electrolyte solution inside the first and second flow paths. The electrode unit includes at least two electrodes disposed in the first and second flow paths respectively. When the pair of electrodes is driven to electrolyze the electrolyte solution, the ion exchange membrane retards the mixing of an anode product and a cathode product produced by electrolyzing the electrolyte solution, such that a liquid having pH gradient is generated inside the first and second flow paths.

22 Claims, 3 Drawing Sheets

MICRO FLOW DEVICE AND METHOD FOR GENERATING A FLUID WITH PH GRADIENT

This application claims the benefit of Taiwan Patent Application Serial No. 96127851, filed Jul. 30, 2007, the subject matter of which is incorporated herein by reference.

BACKGROUND OF THE INVENTION

Field of the Invention

The present invention relates to a micro flow device, and more specifically, to a micro flow device capable of generating a fluid with pH gradient.

Biochips are made of silicon, glasses, or polymers, and are often combined in use with Micro Electrical Machine System (MEMS), semiconductors, chemical analysis, and biochemical technologies. Biochips have been developed in 1990s and are still being heavily researched, but the technology is already viewed as a next generation star product.

Biochips are categorized into two major categories: the first one is Lab-on-a-chip, which integrates processes normally done in labs onto a chip, and the second one is microarray, which collects tens of thousands of samples and stores them in a chip. The field of biochips took a big leap when micro-arrays were used for DNA testing and helped in determining the sequences of DNA. On the other hand, Lab-on-a-chip integrates complex lab procedures onto a single chip, which can be combined with micro-pumps, micro-filters, micro-sensors, and micro-actuators to test samples on the chip. Lab costs and flows are improved greatly this way.

Since DNA sequence has already been determined, proteomes will be next. Development of proteomic chips is the key issue to determine proteomes. Due to the physical and chemical properties of proteomes, proteomes can remain active only if placed in a natural environment and its 3D structure preserved. The result is that proteomes are sensitive to temperature and pH value, and are highly vulnerable to highly acid or base environment. However, with right pH value, proteomes can be very active when being tested. The control of a pH gradient thus becomes a main focus in developing biochip technology.

Traditional methods for controlling the pH gradient consist either using retardation solutions to control the pH value of a solution or by titration. Industrialized pH value control consists using a controller to control the pH value. The retardation solutions can be used to maintain the pH value in a certain range. Some biochips currently use the retardation solutions to control pH value. However, it is difficult to make the retardation solutions, and maintaining the retardation solutions is also a challenge because it is highly susceptible to temperature variations. For titration, when reaching the equivalent point, the pH value may vary violently.

SUMMARY OF THE INVENTION

The present invention discloses a micro flow device capable of generating a fluid with pH gradient and the method for making the same by electrolyzing an electrolyte solution in the micro flow device and retarding the neutralization of anode and cathode electrolytes using an ion exchange membrane.

The present invention discloses a micro flow device capable of generating a fluid with pH gradient, the device comprising a first substrate, a second substrate, an ion exchange membrane, and at least an electrode unit. The first substrate comprises a first flow path, and the second substrate comprises a second flow path and is located corresponding to the first substrate. The ion exchange membrane is located in between the first substrate and the second substrate for separating an electrolyte solution in the first flow path and the second flow path. The electrode unit comprises at least two electrodes, one being disposed in the first flow path and the other one being disposed in the second flow path.

The present invention also discloses a method for generating a fluid with pH gradient, the method comprising: (a) providing a first substrate having a first flow path and a second substrate having a second flow path respectively, the first flow path and the second flow path being separated by an ion exchange membrane and having at least one electrode unit comprising at least two electrodes, one in the first flow path and the other in the second flow path; (b) placing an electrolyte solution in the first flow path and the second flow path; and (c) driving the electrode unit to electrolyze the electrolyte solution to form a fluid with pH gradient when the ion exchange membrane retards the neutralization of the electrolyzed electrolyte solution.

DETAIL DESCRIPTION OF THE INVENTION

The micro flow device capable of generating a fluid with pH gradient of the preferred embodiment of the present invention generates the fluid with pH gradient by electrolyzing the electrolyte solution in the flow path and by retarding the neutralization of the acid and basic solutions using an ion exchange membrane to form the fluid with pH gradient.

Figure 1A:
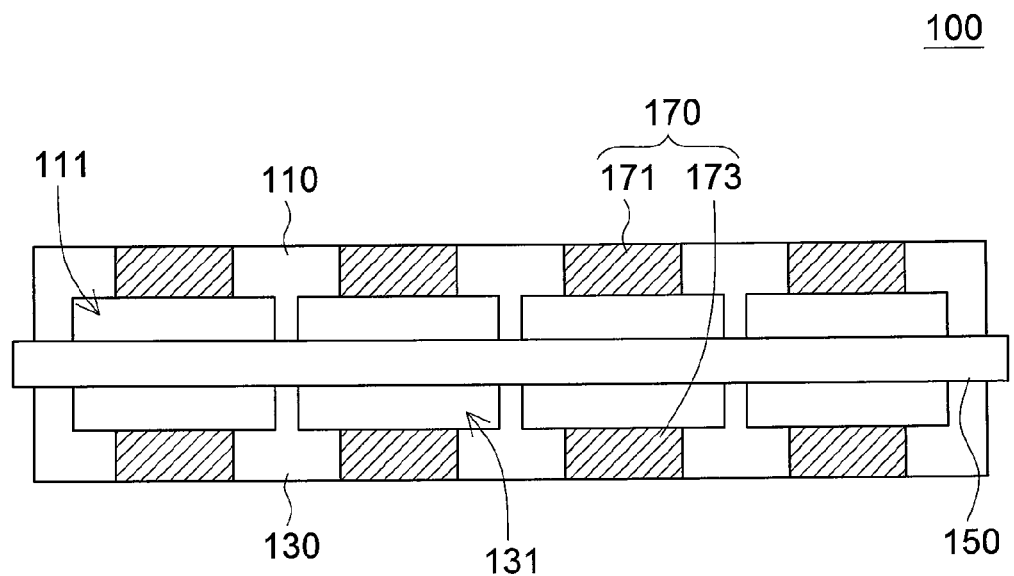
FIG. 1A is an exemplary micro flow device of the present invention capable of generating a fluid with pH gradient.
Figure 1B:
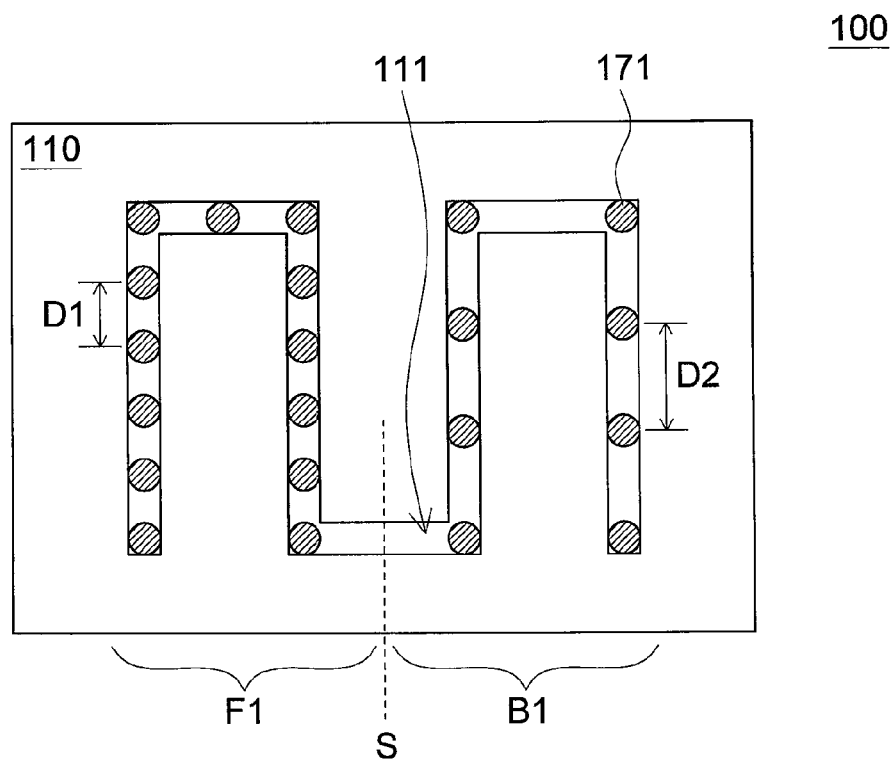
FIG. 1B is the top view of the micro flow device in FIG. 1A.

Referring to FIGS. 1A and 1B, FIG. 1A depicts an exemplary micro flow device capable of generating a fluid with pH gradient, and FIG. 1B is the top view of the micro flow device in FIG. 1A. The micro flow device 100 comprises a substrate 110, a second substrate 130, an ion exchange membrane 150, and at least one electrode unit. The currently embodiment describes a plurality of electrode units 170 disposed on the first substrate 110 and the second substrate 130. The first substrate 110 comprises a first flow path 111. The second substrate 130 comprises a second flow path 131. The second flow path 131 is disposed corresponding to and has substantially the same shape as the first flow path 111. An electrolyte solution (not shown) is in the first flow path 111 and the second flow path 131. In the currently embodiment, an inert electrolyte solution is used, such as $K_2SO_4$ solution. When electrolyzing the inert electrolyte solution, the following reaction will occur at the anode and cathode respectively:

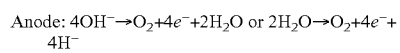

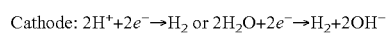

Based on the above reactions, a gas of $O_{2(g)}$ is formed at the anode and a gas of $H_{2(g)}$ is formed at the cathode when the electrolyte solution is electrolyzed. As a result, the solution close to the anode is acid and the solution close to the cathode is base. Because the first substrate 110 and the second substrate 130 are attached to each other with the ion exchange membrane 150 in between, the first flow path 111 and the second flow path 131 are separated by the ion exchange membrane 150. The ion exchange membrane 150 selectively allows ions to pass through, hence retards the neutralization of the acid solution and the base solution. The ion exchange membrane 150 may be a proton exchange membrane, a multi-ion exchange membrane, or an ion exchange membrane for fuel cell batteries. A proton exchange membrane is selected to be the ion exchange membrane 150 in the current embodiment.

The electrode unit 170 comprises a first electrode 171 and a second electrode 173 being disposed in the first flow path 111 and the second flow path 131 respectively. The electrode unit 170 applies voltages of different polarities to the first electrode 171 and the second electrode 173. In the current embodiment, the first electrode 171 and the second electrode 173 are disposed at an equal distance away from the ion exchange membrane. However, various distances may be used depending on the circumstances. In the currently embodiment, a plurality of electrode units 170 are disposed at unequal distances along the direction of the first flow path 111 and the second flow path 131, as shown in FIG. 1B. However, the electrode units can also be disposed at an equal distance away in another embodiment.

The micro flow device 100 may further comprise driving unit (not shown). The driving unit may be disposed in the first flow path 111, the second flow path 131, the first substrate 110, or the second substrate 130. The driving unit may also be disposed in the micro flow device 100 according to the structure of the micro flow device 100. The driving unit is for driving the fluid in the flow paths to move. When the driving unit drives the fluid, the electrolyzed anode and cathode solution is driven by the driving unit, and the chance of the anode solution and the cathode solution getting mixed together is reduced. A fluid with better pH gradient can be formed. The driving unit may be a mechanical pump such as a bubble pump, a membrane pump, a diffuser pump, or a rotary pump. The driving unit may also be a sensor driven pump, such as an electrohydrodynamic pump (EHD pump), an electro-osmotic pump, an electrophoretic pump, an electro-wetting pump, or any other hydraulic pumps.

In the current embodiment, the first electrode 171 is anode and the second electrode 173 is cathode. When the electrode unit electrolyzes the electrolyte solution in the first flow path 111 and the second flow path 131, the first flow path 111 and the second flow path 131 are treated as an anode electrolyzing tank and a cathode electrolyzing tank respectively. $K_2SO_4$ solution is used as the electrolyte solution in the current embodiment. Because the first flow path 111 is the anode electrolyzing tank, the electrolyzed solution in the first flow path 111 is an acid solution. Also, since the second flow path 131 is the cathode electrolyzing tank, the electrolyzed solution in the second flow path 131 is a base solution.

The electrolyzed solutions are prevented from being neutralized quickly by the ion exchange membrane 150 to form a fluid with pH gradient.

By designing the micro flow device of the current embodiment of the present invention, a fluid with desirable pH gradient can be obtained by designing the location of the electrodes in the flow paths.

Referring to FIG. 1B, FIG. 1B shows that some of the first electrodes 171 are disposed in F1 of the first flow path 111 at a distance D1 from S, and some of the first electrodes 171 are disposed in B1 of the first flow path 111 at a distance D2. D2 is greater than D1. Each of the second electrodes (see FIG. 1A) is disposed corresponding to one of the first electrodes in the second flow path 131. When electrolyzing the electrolyte solution in the flow paths, the fluid in F1 is more acid or base than the fluid in B1 because the density of the electrodes disposed in F1 is higher than in B1. The fluid in the first flow path 111 in F1 is more acid than in B1. Also, the acidity of the fluid from F1 to B1 forms a pH gradient.

In another embodiment, the distances of the first electrodes 171 and the second electrodes 173 can gradually increase or decrease to form directly a pH gradient.

Figure 2:
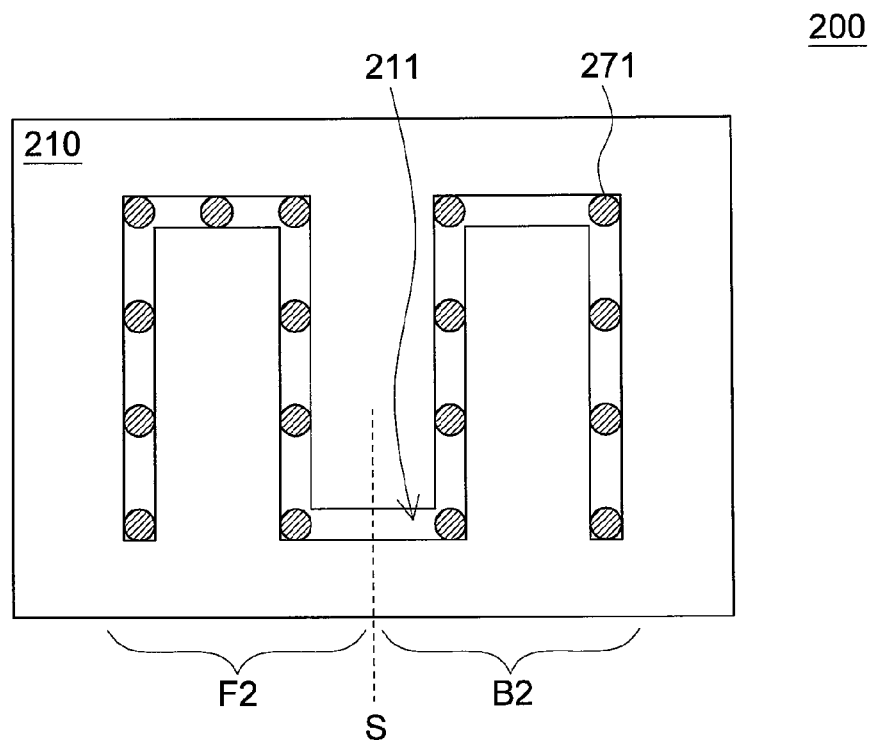
FIG. 2 is the top view of the electrodes disposed on the substrates at an equal distance.

Other than to create the fluid with pH gradient by controlling the location of disposing the electrodes, the fluid with pH gradient can also be formed by controlling the voltages of the electrodes. Referring to FIG. 2, FIG. 2 is the top view of a micro flow device where the electrodes are located at an equal distance away on the substrates. As shown in FIG. 2, the first electrodes 271 are disposed at an equal distance in the first flow path 211, and the second electrodes (not shown) are disposed corresponding to the first electrodes 271 in the second flow path (not shown). The electrodes disposed in F2 have a voltage V1 and the electrodes disposed in B2 have a voltage V2. V1 is greater than V2. The fluid in F2 is more acid or base than the fluid in B2. The fluid from F2 to B2 forms a pH gradient.

By assigning each electrode in the flow path with different voltages, such that the voltages gradually increase or decrease from one end to the other end, a pH gradient with a variety of characters may be obtained. This change of voltages may also be applied to the micro flow device in the previous embodiment depicted in FIGS. 1A and 1B.

A pH meter may also be used to detect the acid and base value in the flow paths. The voltages of the electrodes may be adjusted according to the acid and the base levels detected. A more precise pH gradient can be formed by timely adjusting the voltages to control the acid and base value.

Figure 3:
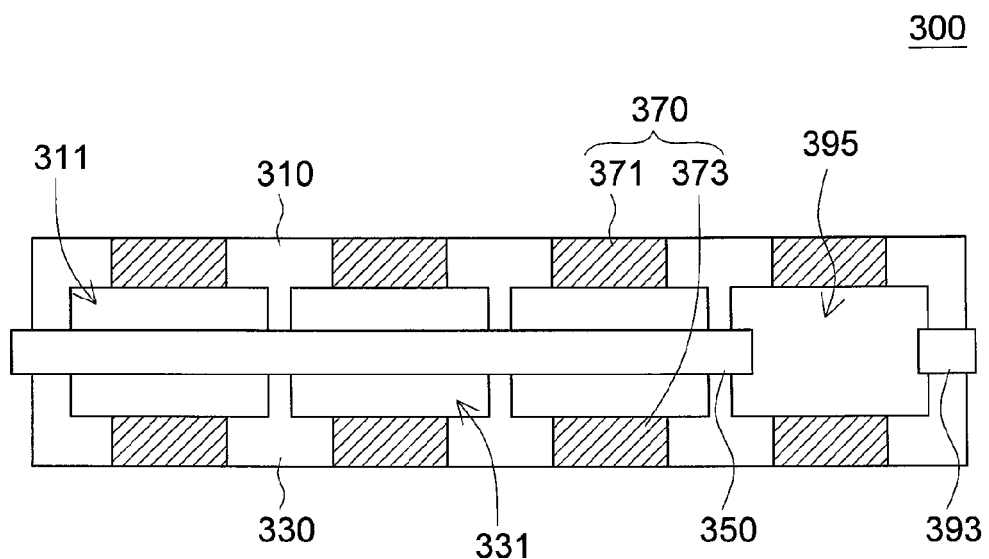
FIG. 3 depicts the first flow path and the second flow path being connected to each other.

In the current embodiment, the first flow path 111 and the second flow path 131 are two independent paths that are not connected. In another embodiment, the first flow path and the second flow path may also be connected. Referring to FIG. 3, FIG. 3 depicts a micro flow device with a first flow path and a second flow path that are connected. The first flow path 311 and the second flow path 331 are connected through connecting point 395 on a side of the first substrate 310 and a side of the second substrate 330. An attaching point 393 corresponding to the connecting point 395 connects the first substrate 310 and the second substrate 330.

When electrolyzing the fluid in the flow path, the pH values vary according to the position in the flow path. If the first electrode 371 is anode and the second electrode 373 is cathode, the fluid is close to neutral at the connecting point 395 since there is no ion exchange membrane 350 to retard the neutralization and the acid and base fluids are mixed directly. When the location is further away from the connecting point 395, there is less chance for the anode product and the cathode product to mix and hence the fluid is more acid or base. A fluid with pH gradient is thus formed.

Figure 4:
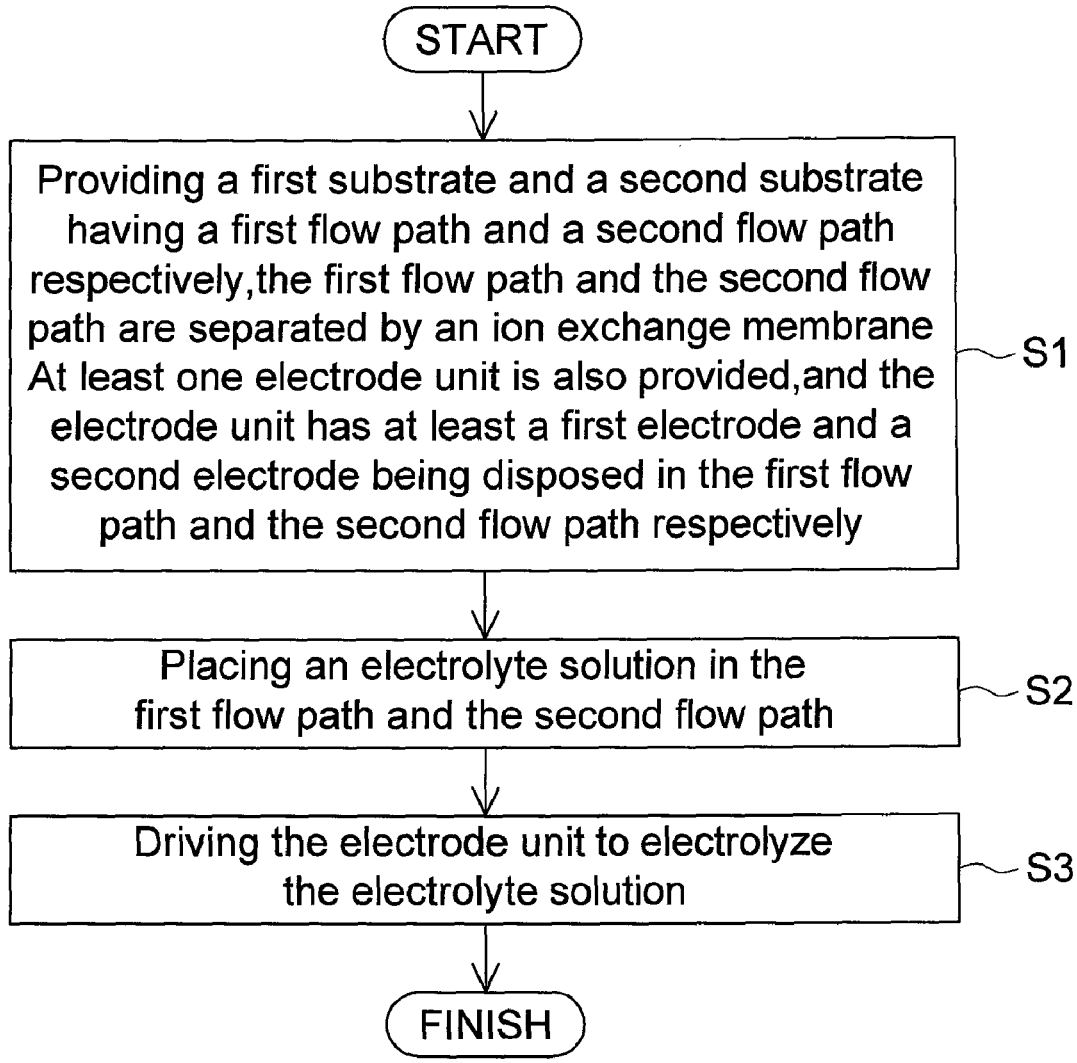
FIG. 4 is an exemplary flow chart of the method for generating a fluid with pH gradient of the embodiment of the present invention.

A method for generating a fluid with pH gradient is disclosed according to the micro flow device capable of generating the fluid with pH gradient mentioned above. Referring to FIG. 1A and FIG. 4, FIG. 4 is a flow chart for the method of generating a fluid with pH gradient according to the present embodiment of the present invention.

In step S1, a first substrate 110 and a second substrate 130 are provided. The first substrate 110 comprises a first flow path 111 and the second substrate 130 comprises a second flow path 131. The first flow path 111 and the second flow path 131 are separated by an ion exchange membrane 150. At least one electrode unit 170 is also provided. The electrode unit 170 comprises at least one first electrode 171 and at least one second electrode 173. The first electrode 171 is disposed in the first flow path 111 and the second electrode 173 is disposed in the second flow path 131.

In step S2, an electrolyte solution is placed in the first flow path 111 and the second flow path 131.

In step S3, the electrode unit 170 is driven to electrolyze the electrolyte solution in the first flow path 111 and the second flow path 131. The electrode unit 170 is driven by a power supply device such as a DC generator, a DC supplier, or a battery. Also, the pH gradient of the fluid can be changed by changing the voltages of the electrode unit 170. Hence, step S3 may also include the step of controlling the voltages, such as changing the voltages periodically, or manually or automatically adjusting the voltages according to the pH values of the fluid.

Because electrolysis bubbles are formed on the first electrode 171 and the second electrode 173 when the electrolyte solution is electrolyzed, the electrolysis bubbles can be used to help moving the fluid in the flow path. Step S3 may also include the step of controlling the rate, number, and order of the electrolysis bubbles being formed to further control the pH gradient of the fluid. For instance, by changing the current of the electrode unit 170, the duration of electrolyzing, or the order of initiating the electrode unit 170, the pH gradient of the fluid can be controlled.

A fluid with better pH gradient can be obtained by moving the fluid along in the flow paths. In the current embodiment, a step of moving the fluid along the flow paths may also be included. The step may be designing the fluid in the first flow path 111 and the second flow path 131 to move in the same direction, or to move in different directions. Of course, the step may also include controlling the speed and flow rate of the fluid in the first flow path 111 and the second flow path 131.

In the above embodiments, the micro flow device capable of generating a fluid with pH gradient and the method of generating the same are accomplished by electrolyzing an electrolyte solution in the flow paths of the micro flow device and retarding the neutralization of the fluid with an ion exchange membrane. The fluid with desired pH gradient can be obtained by controlling the location of the electrode unit, method of moving the solution, or rate of forming electrolysis bubbles. There are several advantages to these embodiments:

1. Distance is usually an issue for electrolyzing, however, in the current embodiment electrolyzing is done in a micro flow device where the diameter is small; electrolyzing can be done using relatively small voltages.

2. Because the pH gradient is generated under the scale of the micro flow device, there may be many applications. The micro flow device of the present invention can be applied in an optical disc or a biochip for controlling the pH value of a proteomic chip or a DNA chip. Since there is no need for a retardation solution, the results are more accurate.

3. The micro flow device is capable of generating a fluid with various pH values. This saves a lot of time and cost to produce different fluids with different pH values separately.

4. The embodiment of the present invention is capable of controlling the pH values of the fluid in real time, which is useful to pH sensitive processes such as for growing micro organisms or enzymes.

5. The fluid with pH gradient generated in the current embodiment of the present invention is not temperature sensitive and can be adjusted accordingly. Hence, the present invention can be applied to applications that might generate heat in the process.

6. The structure of the micro flow device of the current embodiment of the present invention is not complex. The micro flow device can be manufactured using simple manufacturing processes and can be fully integrated on a single chip. This greatly increases the applications of the micro flow device in many industries.

While the invention has been described with reference to exemplary embodiments, it is to be understood by those skilled in the art that various changes may be made and equivalents substituted for elements thereof without departing from the scope of the invention. On the contrary, it is intended to cover various modifications and similar arrangements and procedures, and the scope of the appended claims therefore should be accorded the broadest interpretation so as to encompass all such modifications and similar arrangements and procedures.

What is claimed is:

1. A micro flow device comprising:
a first substrate, having a first flow path;
a second substrate, having a second flow path, disposed corresponding to the first substrate;
an ion exchange membrane, disposed between the first substrate and the second substrate for separating an electrolyte solution in the first flow path and the second flow path; and
at least two electrode units, wherein each of the electrode units comprises a first electrode and a second electrode respectively disposed in the first flow path and disposed in the second flow path;
wherein when the at least two electrode units are driven to electrolyze the electrolyte solution, the first electrodes are of the same charge type, the second electrodes are of the opposite charge type to the first electrodes, the ion exchange membrane retards the mixing and neutralization of an anode product and a cathode product generated by electrolyzing the electrolyte solution, and a first fluid and a second fluid are generated in each of the first flow path and the second flow path with pH gradient along a direction of the first flow path and the second flow path respectively.

2. The micro flow device of claim 1, further comprising at least one driver for driving the first fluid and the second fluid.

3. The micro flow device of claim 2, wherein the driver is a mechanical micro pump.

4. The micro flow device of claim 2, wherein the driver is a sensor-driven micro pump.

5. The micro flow device of claim 1, wherein the ion exchange membrane is a multi-ion exchange membrane.

6. The micro flow device of claim 1, wherein the ion exchange membrane is a proton exchange membrane.

7. The micro flow device of claim 1, wherein the ion exchange membrane is an ion exchange membrane for fuel cell.

8. The micro flow device of claim 1, wherein the first flow path and the second flow path are connected through a side of the first substrate and a side of the second substrate.

9. The micro flow device of claim 1, wherein the first electrode and the second electrode of each electrode unit are disposed in the first flow path and the second flow path at the same distance away from the ion exchange membrane respectively.

10. The micro flow device of claim 1, wherein the first electrodes are disposed along the direction of the first flow path, and the second electrodes are disposed along the direction of the second flow path.

11. The micro flow device of claim 10, wherein more than two of the electrode units are disposed by spacing the adjacent electrode units apart with an equal distance.

12. A method for generating pH gradient, the method comprising:
(a) providing a first substrate having a first flow path, a second substrate having a second flow path and at least two electrode units, wherein the first flow path and the second flow path are separated by an ion exchange membrane, each of the electrode units comprises a first electrode and a second electrode, the first electrodes are disposed in the first flow path, and the second electrodes are disposed in the second flow path;
(b) placing an electrolyte solution in the first flow path and the second flow path; and
(c) forming a first fluid and a second fluid each with pH gradient respectively along a direction of the first flow path and the second flow path by driving the electrode units to electrolyze the electrolyte solution when the ion exchange membrane retards the neutralization of the electrolyzed electrolyte solution,
wherein when driving the electrode units, the first electrodes are of the same charge type, and the second electrodes are of the opposite charge type to the first electrodes.

13. The method for generating pH gradient of claim 12, wherein (c) comprises providing a direct current voltage to the electrode units for electrolyzing the electrolyte solution.

14. The method for generating pH gradient of claim 12, wherein (c) further comprises adjusting the number of electrolysis-bubbles in the first flow path and the second flow path to change pH gradients of the first fluid and the second fluid.

15. The method for generating pH gradient of claim 12, wherein (c) further comprises adjusting the speed of generating electrolysis-bubbles to change pH gradients of the first fluid and the second fluid.

16. The method for generating pH gradient of claim 12 further comprising driving the first fluid and the second fluid respectively in the first flow path and the second flow path to move.

17. The method for generating pH gradient of claim 12, wherein the first electrodes are disposed along the direction of the first flow path and the second electrodes are disposed along the direction of the second flow path.

18. The method for generating pH gradient of claim 17 further comprising driving the electrode units at different times so electrolysis bubbles generated in the first flow path and the second flow path are in different orders to form the first fluid and the second fluid each with pH gradient.

19. The method for generating pH gradient of claim 17, further comprising varying the driving voltages of the electrode units according to their locations to change pH gradients of the first fluid and the second fluid.

20. The method for generating pH gradient of claim 17, further comprising the driving voltage of the electrode units having a gradient variation to change pH gradients of the first fluid and the second fluid.

21. The micro flow device of claim 1, wherein the first electrodes and the second electrodes have the same shape.

22. The method for generating pH gradient of claim 12 further comprising forming electrolysis-bubbles on the first electrodes and the second electrodes when the electrolyte solution being electrolyzed, wherein electrolysis-bubbles help moving the first fluid and the second fluid in the first flow path and the second flow path, respectively.

* * * * *